United States Patent [19]

Brown J. Steven et al.

[11] Patent Number: 4,471,771

[45] Date of Patent: Sep. 18, 1984

[54] ORAL WEIGHT CONTROL DEVICE

[76] Inventors: Brown J. Steven, 1071 University Village, Salt Lake City, Utah 84108; Charles E. Comstock, 5871 Ayrshire Dr., Murray, Utah 84107

[21] Appl. No.: 331,914

[22] Filed: Dec. 18, 1981

[51] Int. Cl.³ .............................................. A61F 5/46
[52] U.S. Cl. ............................... 128/136; 128/132 R; 128/155
[58] Field of Search ...................... 128/136, 137, 133; 433/7

[56] References Cited

U.S. PATENT DOCUMENTS

| 1,582,570 | 4/1926 | Brust | 433/7 |
| 2,037,079 | 4/1936 | Locke | 128/136 |
| 2,077,245 | 4/1937 | Locke | 128/136 |
| 3,132,647 | 5/1964 | Corniello | 128/136 |
| 4,028,808 | 6/1977 | Schwartz | 433/7 |
| 4,373,913 | 2/1983 | McAndrew | 433/7 |

Primary Examiner—C. Fred Rosenbaum
Assistant Examiner—C. W. Shedd
Attorney, Agent, or Firm—Thorpe, North & Western

[57] ABSTRACT

An oral weight control apparatus and method adapted to block solid foods from entering the stomach of a user thereof, while at the same time allowing the user to freely move his tongue and jaws, to talk, to breathe, to drink fluids, and to participate in other desirable activities without the presence of the apparatus being visible or otherwise made known to anyone other than the user. The apparatus includes a guard, net, or other sieve-like blocking means that is secured inside the mouth of the user. Liquids and finely ground foods may freely pass through the guard or sieve but solid foods may not. In the preferred embodiment, the blocking means functions as a one-way valve, blocking solid foods from entering the stomach through the mouth but allowing food within the stomach to pass back out through the mouth (as would occur, for example, during regurgitation). The method includes mounting such an apparatus within the mouth in order to constrain the user to follow a suitable diet comprised of liquids and finely ground foods having a desired nutrient level.

8 Claims, 9 Drawing Figures

ORAL WEIGHT CONTROL DEVICE

BACKGROUND OF THE INVENTION

This invention relates to an apparatus and method for weight control, and more particularly, for an apparatus adapted to be fitted within the mouth of a user so as to control the amount of solid food that the user may intake into his or her digestive system.

Methods and apparatus for controlling weight are known in the art. Known methods include dieting, exercising, body wrapping, special medications, and the like. The most effective method of weight control is, of course, to merely limit the amount of calories that are taken into one's digestive system. Thus, dieting, and variations thereof, including fasting, are perhaps the most wide spread and well known methods of weight control. Because a large number of calories are ever present in solid foods, many diets prescribe only liquids. Such liquids are typically controlled to contain a needed amount of nutrients and calories.

Unfortunately, not everyone who has decided to follow a liquid diet is able to do so. Habit, lack of will power, peer pressure, and physiological and/or psychological disorders, are only some of the stumbling blocks that may prevent a person who wants and needs to follow an appropriate liquid diet from doing so.

In order to overcome these and other stumbling blocks, it is known in the art to take "drastic" measures in order to force a person to lose weight. Such measures have included major surgery (e.g., to staple the stomach in order to reduce its size or to block the amount of food that may enter or leave the stomach, or to shorten the length of the intestines). The risks associated with such major surgery are legion, and these risks (which have resulted in many deaths), as a general rule, far outweigh the benefits that the surgery may ultimately bring. Thus, major surgery is not a viable alternative to most people who desire or need to lose weight. It is well known that the purpose of such surgery is to reduce stomach or intestine volume and thereby develop a sense of being full after eating less food. Published research has shown that even under normal conditions, however, there is a time lag between the entry of food into the digestive tract and the assimilation of nutrition into the blood stream. For example, it takes approximately twenty minutes from the time that the food reaches the stomach lining for it to be broken down so that it can be absorbed into the blood stream. This then carries the message of nourishment to the hunger centers of the brain, triggering a response of being full. Therefore, the rapid ingestion of foods until the hunger sensation is satisfied will invariably lead to excessive calorie intact. Additional information regarding this phenomenon can be found in *Act Thin, Stay Thin,* Dr. Richard B. Stuart, W. W. Norton & Company, Inc., New York (1977). For these reasons, it is generally recommended that solid foods be well chewed, so that the digestive process can be accelerated, in addition to slowing down the actual rate of food consumption. Obviously, the smaller the particles of food are, the more rapid is the assimilation of nutrition into the blood stream. Therefore, the foregoing methods have shown some effectiveness for weight loss.

Another method known in the art for losing weight—and particularly adapted to restrict a person to a liquid diet—is to install apparatus in the mouth of the user that prevents the user from opening his mouth. This method—generally referred to as "wiring one's mouth shut"—is very effective. That is, when this method is pursued, the jaw bones are physically constrained from opening any farther than is absolutely necessary in order to allow liquids to enter the mouth. Thus, the user is forced to take nothing but liquids for food, and the content of these liquids may be selectively controlled to provide a proper calorie and nutrient level.

Although wiring one's mouth shut is very effective, it is also frought with difficulties and undesirable side effects. First, wiring the mouth shut prevents the person from talking in a normal fashion. This, in turn, may cause social inhibitions. Moreover, the wires used to perform the wiring function are generally visible to others, thus creating an unsightly scene for others to observe whenever they look at the individual. This also could cause serious social problems.

Second, wiring the mouth shut precludes proper oral hygiene. Teeth cannot be brushed, flossed, or rinsed in an effective manner. Thus, tooth decay, gum diseases, and bad breath are prospective side effects that may attend having one's mouth wired shut.

Third, wiring the mouth shut imparts a claustrophobic feeling to the user, causing much frustration due to his or inability to talk, yawn, or to otherwise properly exercise the jaw and tongue muscles. Such a situation may cause both psychological as well as physiological problems for the user.

Fourth, a definite health hazard exists if the mouth is wired shut and the user has a need to regurgitate (throw-up). If the emergent material is not allowed to freely exit through the mouth at a rather rapid volumetric flow rate, then the regurgitated material may be forced into the respiratory system, including the lungs. Such a situation could cause serious injury, even death.

Fifth, "wiring one's mouth shut" restricts the persons to a diet consisting strictly of liquids which must typically be administered through a large syringe or similar method. Such a "pure" liquid diet lacks food fiber, a nutrient necessary for good health.

SUMMARY OF THE INVENTION

It is therefore an object of the present invention to provide an oral weight control apparatus adapted to be installed in a user's mouth to impede the ingestion of solid foods, while at the same time allowing the user to freely ingest liquids and small food particles.

It is a further objective of the present invention to provide such an oral weight control apparatus that allows the user to freely talk and move his jaw and tongue muscles in a normal fashion.

It is still a further object of the present invention to provide such an oral weight control device that allows the user to readily brush, floss, and rinse his teeth in order to maintain proper oral hygiene.

Still a further object of the present invention, in accordance with a preferred embodiment thereof, is to provide such an oral weight control apparatus that readily allows regurgitated matter to freely pass from the stomach out through the mouth, yet blocks solid foods from entering the stomach through the mouth.

An additional object of the present invention is to provide such an oral weight control device that is generally non-visible to those who look upon the user thereof, thereby allowing the user to use the apparatus without having its use made known to others.

A further object of the oral weight control device of the present invention is to allow all necessary food nutrients, including food fiber, to be taken into the digestive system.

The above and other objectives of the present invention are realized in an embodiment that includes a sieve-like guard that is secured inside the user's mouth and positioned rearwardly therein so as to not be generally visible from the front of the mouth. Moreover, the guard is positioned above the tongue so as to not unduly restrict talking or other jaw and tongue movement. In the preferred embodiment, the guard is pivotally secured to a brace, band, or stirrup fastened to the upper teeth. Gravity (or other force means) are used to cause the guard to always pivot to a closed position, which closed position guards the entrance to the esophagus. That is, all food entering the esophagus must pass through the meshed openings of the guard when the guard assumes its closed position. However, should a volume of food matter be expelled from the stomach, as would occur during regurgitation, such food material would, upon striking the back side of the guard, readily move it to its open position, thereby allowing the regurgitated matter to freely pass out of the mouth.

The oral weight control device of the present invention thus restricts the ingestion of food matter into the digestive system to liquids and finely ground foods. However, the user is free to talk, yawn, or exercise his jaw and tongue muscles in whatever manner is desired. Further, oral hygiene can be observed at all times. Also, those around the user of the device need not be aware that the device is being used. Moreover, should the user become ill and need to regurgitate, the device is adapted to allow regurgitated matter to freely exit from the mouth.

BRIEF DESCRIPTION OF THE DRAWINGS

The above and other objects, features, and advantages of the invention will be more apparent from the following more particular description presented in connection with the accompanying drawings, in which.

DETAILED DESCRIPTION OF THE INVENTION

The invention disclosed herein is best understood by reference to the drawings, wherein like numerals will be used to describe like parts throughout.

Figure 1:
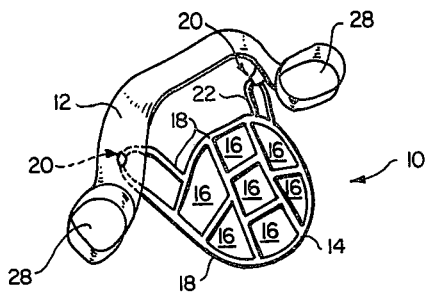
FIG. 1 is a frontal perspective view of one embodiment of the invention as it would appear outside of the mouth.
Figure 2:
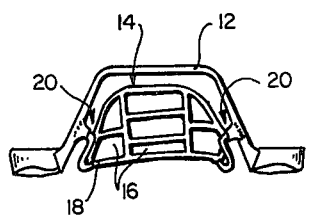
FIG. 2 is a back view of FIG. 1, depicting how the guard is pivotally mounted to an upper support brace.

In FIG. 1, a frontal perspective view of one embodiment of an oral weight control device 10 is shown as it would appear outside of the mouth. This embodiment comprises two basic elements: an upper support brace 12, and a guard 14. The guard includes openings 16 therein that allow liquids and finely ground foods to freely pass therethrough. The size of these openings 16 may be adjusted depending on the needs of a particular user. In FIG. 1, for example, the guard 14 is realized from relatively stiff wires or tubes 18 that are bonded or otherwise secured to each other in a lattice-type framework. Thus, with the openings 16 present within the guard 14, the guard functions similar to a sieve—allowing liquids and finely ground materials to freely pass therethrough, yet blocking or preventing solid foods having a size larger than the meshed openings 16 from passing therethrough. This blocking action impedes ingestion of large food particles, allowing more thorough mastication thereof by the rear teeth.

The guard 14 is pivotally mounted to the upper support brace 12 at pivot points 20. This pivot mount is preferably adapted to allow the guard 14 to freely pivot with respect to the support brace 12. Thus, when the apparatus 10 is worn inside of the mouth, the guard 14 freely pivots to its lower or closed position, as shown best in FIGS. 4 and 5A, under the influence of gravity. If desired, a suitable spring 22 could be employed to bias the guard 14 in its closed or lower position. The use of such a spring 22 would maintain the guard 14 in its closed position when the mouth is open and the tongue down regardless of the orientation the user might assume with respect to the gravitational force field. (That is, the spring would prevent the user from circumventing the function of the guard 14 by engaging in such unorthodox practices as eating with his head in an upside down position.) The spring constant associated with the spring 22 would, of course, be selectively chosen such that should food matter be pushed against the back side of the guard 14, as would occur during regurgitation, the spring constant would allow the guard to readily assume its open position.

Figure 3:
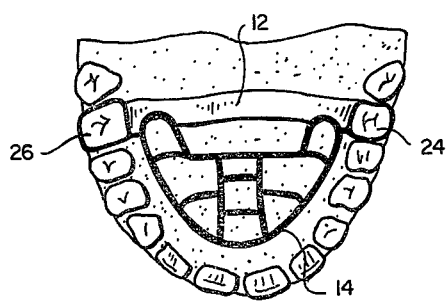
FIG. 3 is a plan view of the upper inside mouth showing how the invention of FIG. 1 may be secured to the upper rear teeth.

The upper support brace 12 is configured to fit against the roof of the user's mouth. Typically, this brace 12 will be secured inside the mouth by looping the ends thereof around upper rear reeth 24 and 26 as shown in FIG. 3. To this end, the upper support brace 12 has loops 28 at respective ends thereof which are adapted to securely fit around teeth 24 and 26. While the upper support brace 12 is shown in the figures as being secured to rear teeth 24 and 26, it is understood that the invention contemplates securing the brace 12 inside of the mouth in whatever fashion may be appropriate for a particular user.

Figure 6A:
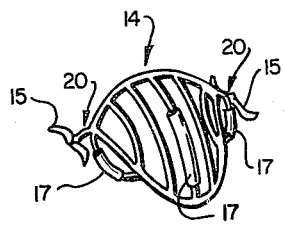
FIG. 6A is a perspective view of another embodiment of the invention that does not use an upper support brace, but wherein the guard is pivotally mounted to stirrups that connect directly to the user's teeth.
Figure 6B:
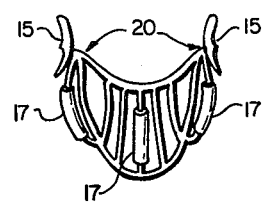
FIG. 6B is a top view of the embodiment of FIG. 6A.

In lieu of the upper support brace 12, it may be desirable to use an embodiment of the invention as shown in FIGS. 6A and 6B. In this embodiment, the guard 14 is pivotally mounted to stirrups 15 at pivot points 20. These stirrups, in turn, may be cemented, or otherwise fastened, directly to the user's teeth. The particular embodiment used (FIG. 1 or FIG. 6A) will depend to a large extent on the size of the user's mouth the presence of various dental work already performed (such as caps, crowns, bridges, etc.), and the potential difficulty of inserting bands 28 between the user's teeth. However, either embodiment serves the same function. The discussion which follows is directed to both the embodiment of FIG. 1, as well as to the embodiment of FIGS. 6A and 6B.

Figure 4:
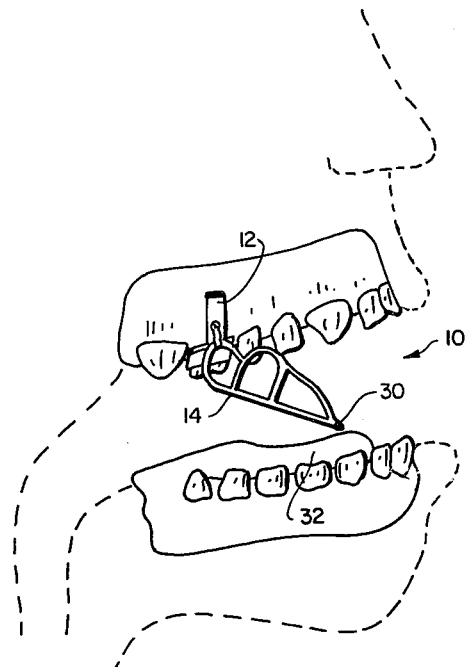
FIG. 4 is a side profile view of the invention as fitted within the mouth of a user thereof.

In FIG. 4, a side profile view of the oral weight control device 10 is shown as it might be worn inside of the mouth of a user. The guard 14 assumes its lower or closed position at all times, causing the tip of the guard, shown at 30, to rest upon the top of the tongue 32. While this configuration may present some mild discomfort to a user for the first few hours of installation, experience has indicated that the user quickly adapts to having the device in his or her mouth and is quickly (within a day or so) able to compensate for the presence of the guard so as to freely talk, move the jaws, tongue, and the like. In this regard, it should be noted that orthodontists have placed a wide variety of appliances and other devices inside of the mouth of their patients for many years. Many of these appliances are very cumbersome and uncomfortable, yet the wearer thereof quickly adapts to their presence and is soon able to function in a nearly normal fashion.

Figure 5A:
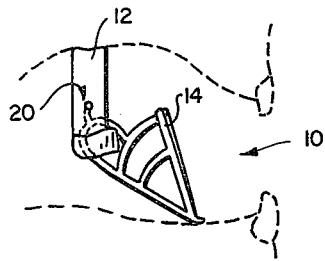
FIGS. 5A and 5B are schematic side views of the invention with the guard pivoted to lower and upper positions respectively, and with the upper and lower boundaries of the user's mouth, including the user's upper and lower front teeth, being illustrated in dashed lines.
Figure 5B:
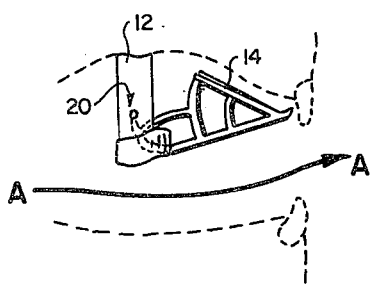

As best seen in FIGS. 4 and 5A, any solid food entering the mouth opening is blocked by the guard 14. Any regurgitated material that is thrown up from the stomach would cause the guard 14 until it is thoroughly chewed to assume its upper or raised position, as shown in FIG. 5B, thereby allowing the regurgitated matter to freely exit the mouth, as represented by the arrow A—A in FIG. 5B. Thus, it is seen that the guard 14 functions similar to a one-way trap door, trapping entry of solid foods passing into the mouth, as shown in FIG. 5A, yet freely allowing the exit of food material from inside of the mouth, as shown at FIG. 5B.

As can be appreciated from the above description, the oral weight control device 10 disclosed herein is a custom made device that is fitted for a specific individual. As such, an oral surgeon, or other qualified dentist, should be consulted and used for the initial installation of the device. Typically, the loops 28 of the upper support brace or band 12 (FIG. 1), or the stirrups 15 (FIG. 6A), will be securely fitted to or around the teeth 24 and 26 so as to prevent removal of the device by the user once it has been installed. However, it is conceivable that the upper band 12, (FIG. 1), or the stirrup 15 (FIG. 6A) while being tightly fitted within the mouth, could nonetheless be detachably fitted therein so as to allow even the user to remove the device should the need arise to do so.

A wide variety of materials could be used to realize the device. For example, chromed steel has been successfully used to realize both the upper support brace 12 and the pivotally mounted guard 14. However, other materials, such as a monofilament (water resistant) nylon material, could be used for the guard 14. Also, there are numerous polymers (plastics) and similar compounds that are commercially available which could provide the needed rigidity for the brace 12 (FIG. 1); guard 14, and stirrups 15 (FIG. 6A). In this connection, it is noted that the brace 12 (FIG. 1) or stirrups 15 (FIG. 6A) and guard 14 could have a certain degree of resiliency associated therewith and still function so as to realize the present invention. In fact, a certain degree of resiliency may be desired. Thus, the guard 14 could be made from a stiff plastic or rubber, or combination of the two; or alternatively, it could be made from a relatively stiff wire that is coated with a suitable rubber or plastic coating. For example, a rubber or latex tubing has successfully been used to cover various wires on guard 14. Such a rubber or latex tubing is shown in FIGS. 6A and 6B as item 17. The primary function served by including tubing 17 in the locations shown (low spots and high spots) is to make the device more comfortable to wear. That is, the tubing 17 acts as a cushion or pad at those spots where the device regularly contacts the mouth.

It should also be noted that the guard 14 could assume a wide variety of shapes which can block passage of large food particles or otherwise retain them at the molars for thorough mastication. The actual shape used would be very dependent upon the needs of the particular user as well as the size and shape of the user's mouth. For example, where a mesh is used the openings 16 could be made very small, in which case a large number of cross braces and supports would be included or added to the lattice structure 18. Alternatively, the openings 16 could be made larger, in which case fewer support members would be used. Further, a slit structure, as shown in the embodiment of FIG. 6A, could be employed, thereby creating long narrow openings through which the food must pass. If a particular patient determines that too much food material is passing by the sides of the guard 14, then appropriate side guards could be fastened to the guard 14 to block such passageways.

Figure 7:
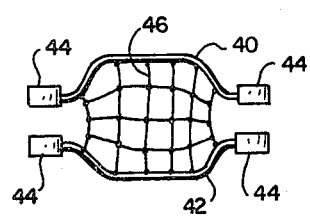
FIG. 7 shows an alternative embodiment of the present invention utilizing upper and lower support braces to which a flexible netting material is attached.

In FIG. 7, a still further alternative embodiment of the invention is shown. This alternative embodiment contemplates the use of an upper support brace 40 secured against the roof of the mouth, and a lower support brace 42 secured across the bottom of the mouth and across the top of the tongue. Appropriate bands or loops 44 could be fastened around appropriate teeth so as to secure the braces 40 and 42 in their desired position. A flexible netting material 46 may then be appropriately secured to the upper and lower support braces 40 and 42. This flexible netting material could be realized from monofilament nylon, meshed metal, or other suitable materials. The material could even be stretchable to a certain extent if desired. Typically, however, it will be fitted loosely between the upper and lower support braces 40 and 42 so as to allow free movement of the jaw muscles and tongue. As with the previous embodiment, the meshed openings within the netting material 46 could be selectively adjusted in order to suit the needs of a particular user. The method used to bond the netting material 46 to the support braces 40 and 42, as well as the method used to bond the fibers of the net material one to another, could be selectively performed so as to allow such bonds to become disengaged if sufficient back pressure is present, as might occur, for example, if a rearward flow of food matter is pushed backwards against the net during regurgitation.

The method of weight control associated with the present invention includes having a device as disclosed herein installed in the user's mouth to force the user to slow the rate of food consumption and to follow an appropriate liquid/ground food diet thereafter it is apparent that this will allow more time for the body to naturally register the sensation of being full or satisfied prior to completion of a meal. As mentioned, it is highly recommended that a user consult with a physician and/or oral surgeon or dentist prior to embarking on a weight control method of this type. The physician, of course, can give proper counsel as to the amount of nutrients and calories which the user should include in his or her diet. The oral surgeon or dentist is needed, of course, to insure that the device is made properly by those trained to make such a device, (i.e., dental lab technicians), and to properly fit and install the oral weight control device 10 within the user's mouth. Obviously, a comfortable fit is essential because the subject weight loss method requires sufficient wearing time to allow natural weight loss to occur.

It should also be appreciated that the present invention can be easily used by those who wear dentures. In such a situation, the guard 14 may be simply pivotally mounted to the denture at an appropriate location. When the denture is removed from the mouth, as is commonly done when sleeping, the guard would also be removed from the mouth.

While the invention herein disclosed has been described by means of specific embodiments and applications thereof, numerous modifications and variations could be made thereto by those skilled in the art without departing from the spirit and scope of the appended claims, the invention may be practiced otherwise than as specifically described herein.

What is claimed is:

1. An oral weight control device for impeding the eating process and slowing down the rate of food consumption to thereby allow the body time to naturally register the sensation of being full prior to completion of a meal, said device comprising:
    an upper support member adapted to be secured to the inside back of the user's mouth;
    a sieve-like guard pivotally coupled in vertical orientation to the support member to allow the guard to raise and lower in response to movements of the user's tongue, said guard having meshed openings therein of a selected size to impede the otherwise unobstructed passage of large food particles;
    said guard including means for positioning a bottom edge thereof at a part of the mouth forward of the support means and near the user's tongue when the device is properly located within the mouth;
    said pivotal attachment providing means for displacement of the guard into a substantially nonblocking position in response to emergent food, thereby preventing possible choking from regurgitated food material.

2. An oral weight control device as defined in claim 1 wherein said guard comprises a lattice of relatively stiff wires bonded to each other in a pattern that realizes the desired meshed openings.

3. An oral weight control device as defined in claim 2 wherein said wires are further bonded in a shape that approximates the inside contour of the user's upper mouth.

4. An oral weight control device as defined in claim 1 further including spring bias means for maintaining said guard in its closed position at all times regardless of the orientation of the user's mouth with respect to a gravitational force field, said spring bias means allowing said guard to assume its open position only in response to a rearward pressure placed thereupon having a force greater than that of said spring bias means.

5. An oral weight control device as defined in claim 1 wherein said food blocking means is detachably secured to the inside of the user's mouth, said detachable securement being realizable only with the aid of another person, such as an oral surgeon or dentist.

6. A method for impeding the eating process and slowing down the rate of food consumption to thereby allow the body time to naturally register the sensation of having hunger satisfied prior to completion of a meal, said method comprising the steps of:
    securing a food blocking device to the teeth inside the mouth of a user without interference to jaw movement, said device being adapted to impede ingesting unchewed solid foods taken into the mouth, yet being unobstructing to emergent foods from the stomach to permit substantially unimpeded passage thereof through the mouth in the event that said user has need to reguritate an amount of ingested food; and
    retaining the device within the mouth for sufficient time to result in loss of weight as part of a weight loss program.

7. A method for assisting a patient to lose weight by impeding the eating process and slowing down the rate of food consumption to thereby allow the body time to naturally register the sensation of having hunger satisfied prior to completion of a meal, said method comprising the securing of a food blocking device to the teeth inside the rear of a patient's mouth without interference to jaw movement, said device being primarily adapted to impede the passage of unchewed solid foods through the mouth to the stomach, yet being nonobstructive to food emergent from the stomach to permit substantially unimpeded passage thereof through the mouth in the event said patient has need to regurgitate an amount of ingested food.

8. A method as defined in claim 7, wherein the food blocking device is secured to the upper rear teeth, thereby forcing the patient to more thoroughly masticate solid food particles by retaining food at the back teeth rather than allowing unobstructed flow of unchewed food into the stomach.

* * * * *